United States Patent
Corato et al.

(10) Patent No.: US 10,583,242 B2
(45) Date of Patent: Mar. 10, 2020

(54) LINE MANAGEMENT DEVICE

(75) Inventors: Craig Douglas Corato, Keller, TX (US); Janalee Marie Corato, Keller, TX (US); Huy Phuong Nguyen, Round Rock, TX (US)

(73) Assignee: JMC GLOBAL TECHNOLOGIES I, L.P., Keller, TX (US)

( * ) Notice: Subject to any disclaimer, the term of this patent is extended or adjusted under 35 U.S.C. 154(b) by 154 days.

(21) Appl. No.: 13/458,635

(22) Filed: Apr. 27, 2012

(65) Prior Publication Data

US 2012/0277682 A1    Nov. 1, 2012

Related U.S. Application Data

(60) Provisional application No. 61/480,172, filed on Apr. 28, 2011.

(51) Int. Cl.
| | | |
|---|---|---|
| *A61M 39/00* | (2006.01) | |
| *A61M 5/14* | (2006.01) | |
| *F16L 3/26* | (2006.01) | |
| *A61M 25/02* | (2006.01) | |
| *A61B 50/20* | (2016.01) | |

(52) U.S. Cl.
CPC .......... *A61M 5/1418* (2013.01); *A61M 25/02* (2013.01); *F16L 3/26* (2013.01); *A61B 50/20* (2016.02); *A61M 2025/024* (2013.01); *A61M 2025/026* (2013.01); *A61M 2025/0206* (2013.01); *A61M 2025/028* (2013.01); *A61M 2025/0213* (2013.01); *A61M 2025/0293* (2013.01); *A61M 2209/082* (2013.01); *Y10S 128/26* (2013.01)

(58) Field of Classification Search
CPC ................ A61M 5/1418; A61M 25/02; A61M 2025/028; A61M 2025/0293; A61M 2025/0206; A61M 2025/026; A61M 2025/024; A61M 2025/0213; F16L 3/26; Y10S 128/26
USPC ....... 604/179, 174, 171, 189, 80; 248/171.1, 248/68.1
See application file for complete search history.

(56) References Cited

U.S. PATENT DOCUMENTS

| | | | | |
|---|---|---|---|---|
| 1,782,404 | A * | 11/1930 | Bowly ...................... | F16L 3/22 24/17 A |
| 2,449,882 | A * | 9/1948 | Daniels ......................... | 604/179 |
| 3,059,645 | A * | 10/1962 | Hasbrouck et al. .......... | 604/179 |
| 4,088,136 | A * | 5/1978 | Hasslinger et al. .......... | 604/179 |
| 4,316,461 | A * | 2/1982 | Marais et al. ................. | 604/179 |
| 4,480,639 | A * | 11/1984 | Peterson et al. .......... | 128/207.18 |
| 4,671,787 | A * | 6/1987 | Widman ....................... | 604/179 |
| 5,084,026 | A * | 1/1992 | Shapiro ................. | A61M 25/02 128/DIG. 15 |
| 5,395,343 | A * | 3/1995 | Iscovich ....................... | 604/179 |

(Continued)

Primary Examiner — Rebecca E Eisenberg
Assistant Examiner — Anh Bui
(74) Attorney, Agent, or Firm — Edwin S. Flores; Daniel J. Chalker; Chalker Flores, LLP

(57) ABSTRACT

The present invention includes a line manager to hold and removably secure within an aperture one or more lines or tubes adjacent to a patient on or near a bed rail, body, or other device. In some embodiments, the line manager is attached to a bed rail of a hospital, or medical bed and may be used to position and label the various tubes or lines going to the patient. The line manager may be made of a flexible material and can be a single use device or a multiple use device.

18 Claims, 7 Drawing Sheets

(56) References Cited

U.S. PATENT DOCUMENTS

| | | | |
|---|---|---|---|
| 5,397,639 A * | 3/1995 | Tollini | 428/343 |
| 5,876,371 A | 3/1999 | Yokoyama et al. | |
| D424,692 S * | 5/2000 | Monaghan et al. | D24/128 |
| 6,315,759 B1 | 11/2001 | Peterson | |
| 6,500,154 B1 * | 12/2002 | Hakky et al. | 604/174 |
| 6,526,981 B1 * | 3/2003 | Rozier et al. | 128/846 |
| 6,544,232 B1 * | 4/2003 | McDaniel | 604/174 |
| 7,255,251 B1 * | 8/2007 | Smith | 224/221 |
| D622,840 S * | 8/2010 | Heitkamp | D24/130 |
| 7,766,289 B2 | 8/2010 | Newkirk et al. | |
| 2005/0137496 A1 * | 6/2005 | Walsh et al. | 600/561 |
| 2006/0064950 A1 * | 3/2006 | Ford | A01K 13/007 54/82 |
| 2009/0105656 A1 * | 4/2009 | Schaeffer | 604/174 |
| 2009/0281502 A1 * | 11/2009 | Heitkamp | 604/179 |
| 2012/0277682 A1 * | 11/2012 | Corato et al. | 604/179 |

* cited by examiner

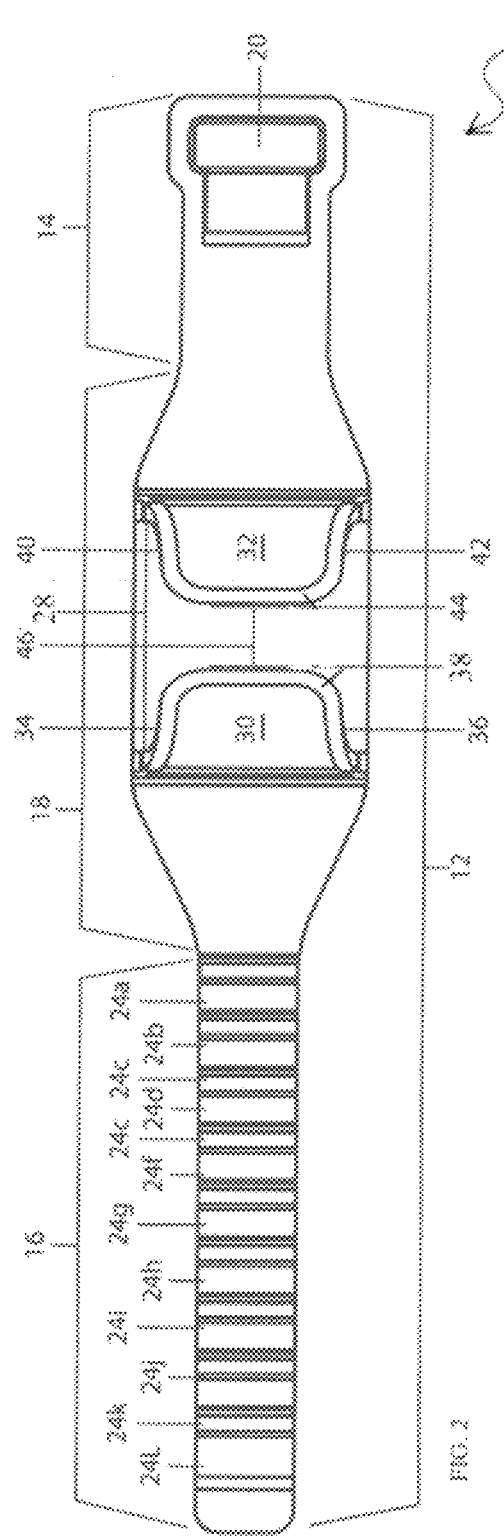
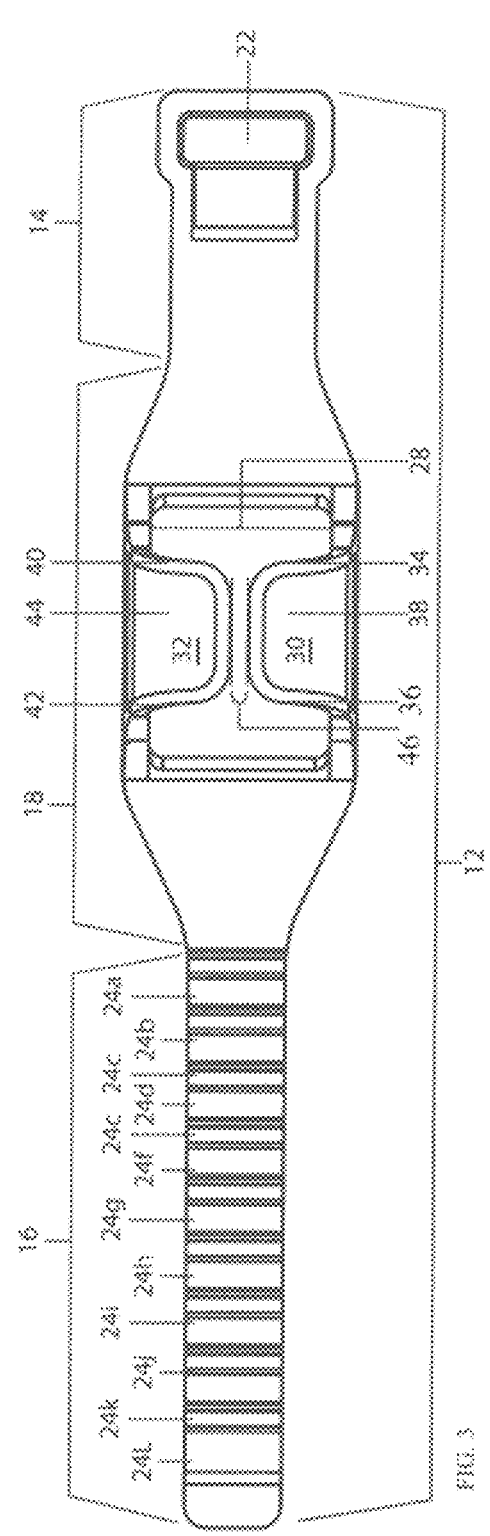

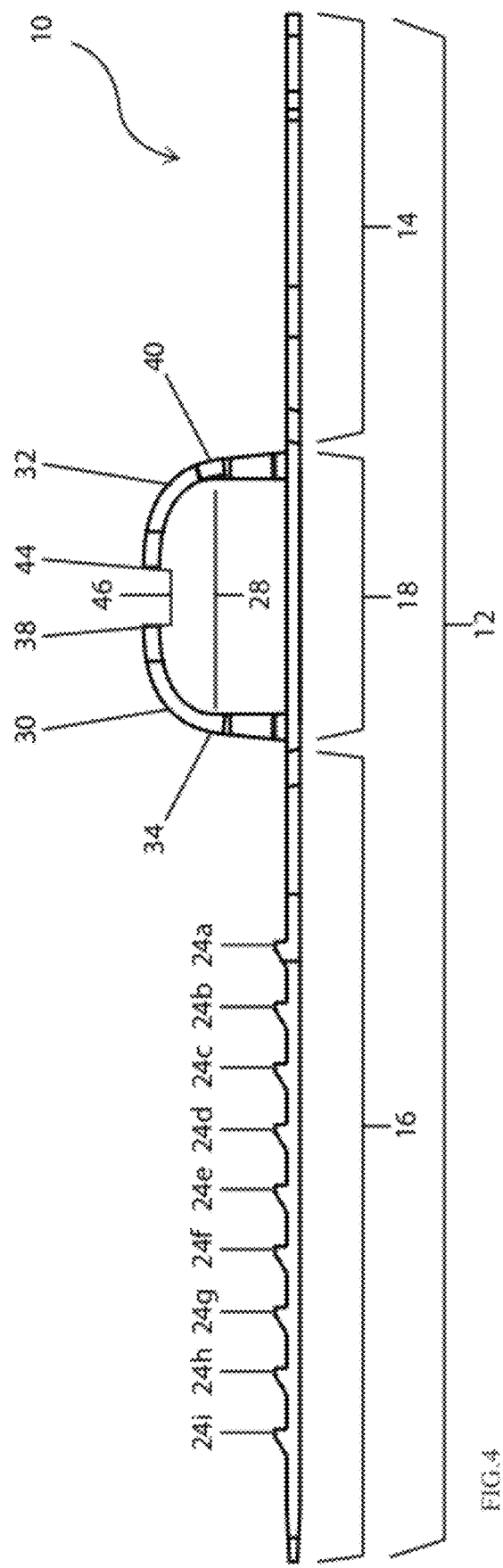
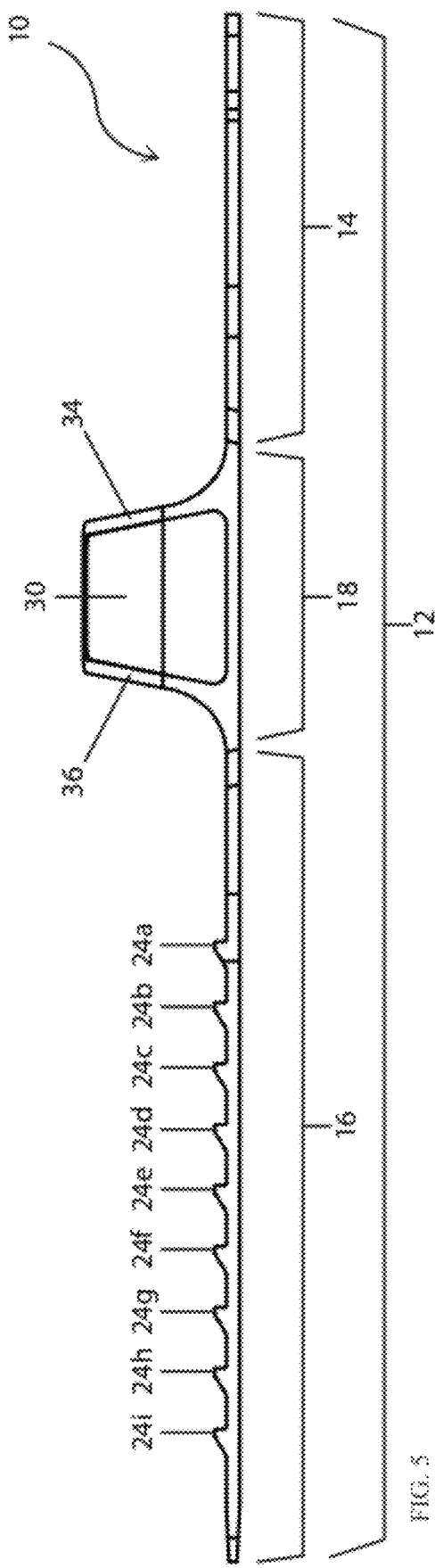

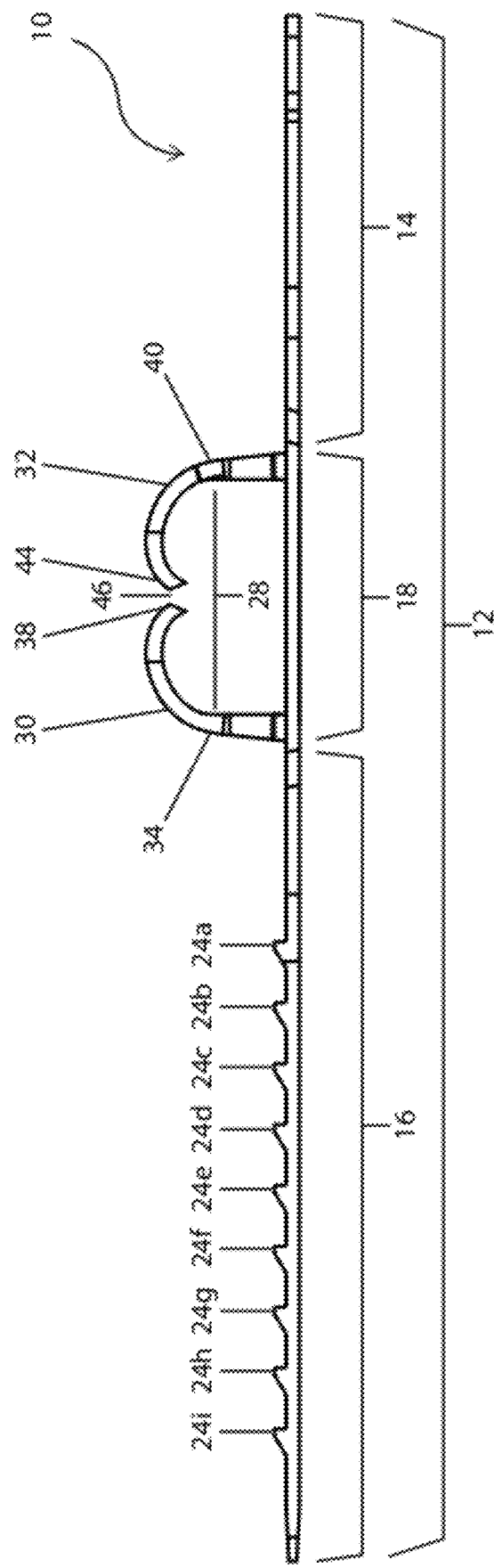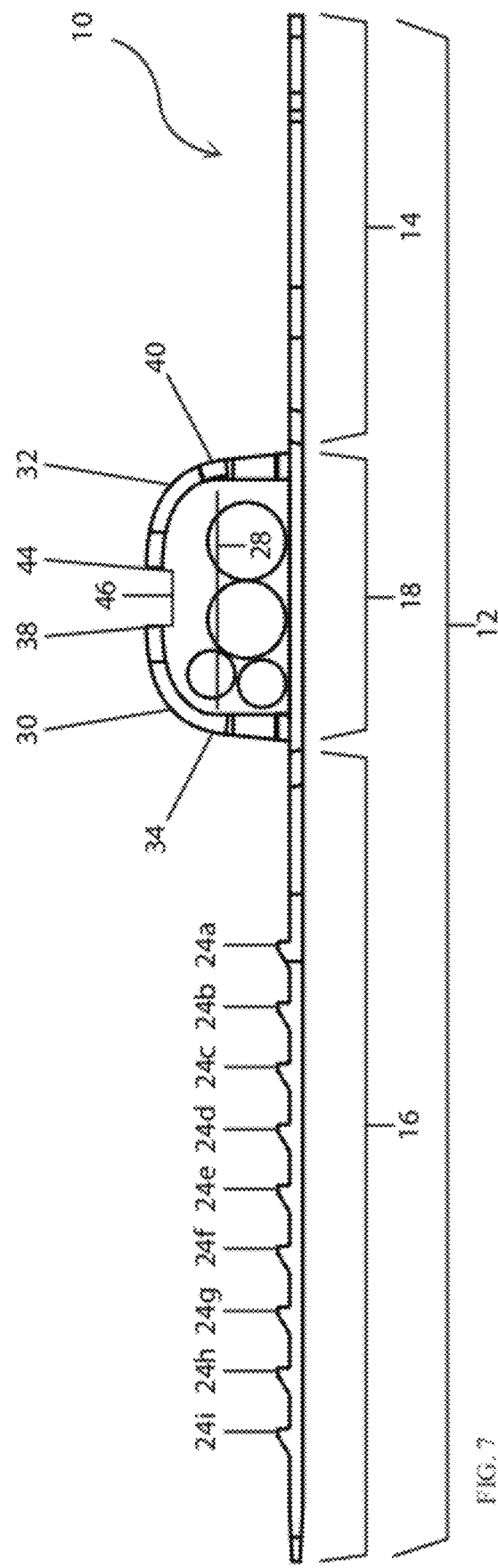

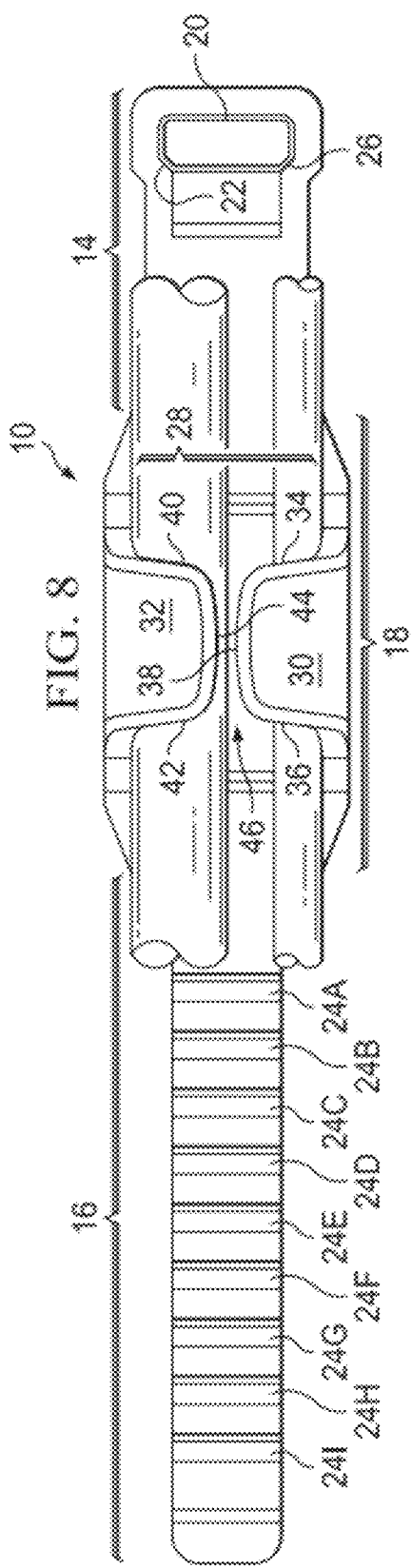

LINE MANAGEMENT DEVICE

CROSS-REFERENCE TO RELATED APPLICATIONS

This application claims priority based on U.S. Provisional Patent Application Ser. No. 61/480,172, filed Apr. 28, 2011. The content of which is incorporated by reference in its entirety.

TECHNICAL FIELD OF THE INVENTION

This invention relates generally to hospital appliances, and, more particularly, to a simple but effective line management device that may be used to organize and protect intravenous lines, and other types of tubing and electrical connections to bedridden patients.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with a line management device to manage one or more care lines to a patient. Patients in hospitals, in home care, etc., often require patient care equipment (e.g., heart monitoring equipment, medical gas delivery equipment, infusion pumps, intravenous bags, equipment monitors, and defibrillators) to be in close proximity and often directly connected to the patient. These intravenous lines, cables, wires and tubes extend from the equipment to the patient and dangle or hang without intermediate support. Many of these lines are put into place or connected to the patient's body prior to the patient being transported. As such, the intravenous lines, cables, wires, and tubes are intertwined, displaced, or entangled, requiring careful tracing to determine the identity of each line, thereby compromising the ability of the attending caregivers to adequately treat the patient. Often these lines are secured to a patient support device, a floor, a wall, an equipment support, or other device by a fastener, tape, or other means to prevent unintentional movement of the lines or tubes to prevent tripping, accidental movement or snagging one of the lines.

For example, U.S. Pat. No. 7,766,289 discloses a patient line management device to manage one or more patient care lines. The line management device includes a line manager coupled to a support. The support is adapted to be coupled to a patient support.

For example, U.S. Pat. No. 6,315,759 entitled "Protective Cover for Intravenous Lines and Other Elongated Members," discloses a protective cover used to surround one or more elongated members such as a plurality of intravenous lines. The cover may be used to cover or protect baby crib rails, bicycle frame sections, handles, and other items wherein the cover assumes the form of a generally cylindrical hollow tube composed of a flexible, resilient material such as closed-cell foam. The tube includes a slit running lengthwise down the tube, enabling the tube to be placed around and over the elongated member by spreading the slit to expose a pair of adjacent, opposing surfaces, each with a length equal to the length of the tube and a width equal to the thickness of the wall. The tube preferably further includes means, other than the tube itself, for maintaining the tube in position around the member. In one configuration, the means for maintaining the tube in position around the member includes an adhesive on one or both of the opposing surfaces, which may be covered with a release layer to expose the adhesive. A separate release layer may be used to cover the slit as well. The means for maintaining the tube in position around the member may also include at least one elongated adhesive strip disposed on the inner wall of the tube. When used to cover and protect intravenous lines, the release layer covering the slit, or a portion of the outer wall covered by the release layer may include one or more messages concerning the use, or re-use of the cover.

For example, U.S. Pat. No. 5,876,371 entitled "Intravenous Tube Holder," discloses an intravenous tube holder for use in a trauma unit or similar environment which includes at least one element, each element preferably containing a plurality of tracks, each track being designed to secure a separate intravenous tube, said element further having a writing surface on the same side of the element as the tracks, with a writing surface next to each track for identifying the content and/or other dosage information identifying the contents of the intravenous tube therein. Each element further has a projection on the side opposite the tracks and writing surfaces for attaching the element to a support means. Each element has a male extension and female indent for interconnecting to additional elements so as to accommodate a greater number of intravenous tubes.

SUMMARY OF THE INVENTION

The present invention includes a line manager to hold and removably secure within an aperture one or more lines or tubes adjacent to a patient on or near a bed rail, or other device. In some embodiments, the line manager is attached to a bed rail of a hospital or medical bed, IV poles, any other structure in the room, or body part and may be used to position and label the various tubes or lines going to and from the patient. The line manager may be made of a flexible material and can be a single use device or a multiple use device.

The present invention provides flexible line management device for one or more patient care lines comprising: a flexible strap comprising a proximal end comprising one or more slots positioned through a portion of the proximal end; a body portion connected to the proximal end, wherein the body portion comprises a first curved tab that extends from the body portion and curves towards an adjacent second curved tab that extends from the body portion and curves towards the first curved tab; a channel formed between the first curved tab and the adjacent second curved tab; and a channel aperture formed between a first edge of the first curved tab adjacent a second edge of the adjacent second curved tab to allow access to the channel; a distal end connected to the body portion, wherein the distal end extends through the one or more slots to secure the distal end to the proximal end. One embodiment of the present invention includes a flexible line management device where the flexible strap is rubber and the channel may be parallel to the proximal end or perpendicular to the proximal end. Furthermore in some embodiments, the first curved tab and the adjacent second curved tab overlap.

The present invention provides a line management device for one or more patient care lines comprising: a flexible strap comprising a proximal end comprises a securing mechanism; a body portion connected to the proximal end, wherein the body portion comprises a first curved tab that extends from the body portion and curves towards an adjacent second curved tab that extends from the body portion and curves towards the first curved tab; a channel formed between the first curved tab and the adjacent second curved tab; and a channel aperture formed between a first edge of the first curved tab adjacent a second edge of the adjacent second curved tab to allow access to the channel; a distal end connected to the body portion, wherein the distal end comprises a connection mechanism that engages the securing mechanism to removably secure the proximal end to the distal end.

One embodiment of the present invention includes a flexible line management device where the channel is parallel to the proximal end or perpendicular to the proximal end. The securing mechanism comprises a hook closure and the connection mechanism comprises a loop closure to mate the securing mechanism and the connection mechanism; a loop closure and the connection mechanism comprises a hook closure to mate the securing mechanism and the connection mechanism; a tab closure and the connection mechanism comprises an aperture closure to mate the securing mechanism and the connection mechanism; an aperture closure and the connection mechanism comprises a tab closure to mate the securing mechanism and the connection mechanism; one or more slots closure and the connection mechanism comprises a tab, wherein the tab extends through the one or more slots to secure the securing mechanism and the connection mechanism; a tab closure and the connection mechanism comprises one or more slots, wherein the tab extends through the one or more slots to secure the securing mechanism and the connection mechanism; the tab comprises one or more ridges to frictionally fit the securing mechanism and the connection mechanism.

The present invention provides a method of managing one or more cables or lines for a patient by providing a flexible line management device comprising a flexible strap comprising a proximal end comprising one or more slots positioned through a portion of the proximal end; a body portion connected to the proximal end, wherein the body portion comprises a first curved tab that extends from the body portion and curves towards an adjacent second curved tab that extends from the body portion and curves towards the first curved tab; a channel formed between the first curved tab and the adjacent second curved tab; and a channel aperture formed between a first edge of the first curved tab adjacent a second edge of the adjacent second curved tab to allow access to the channel; a distal end connected to the body portion; extending the flexible line management device around an object; connecting the distal end through the one or more slots to secure the distal end to the proximal end; and securing one or more cables or lines through the channel aperture into the channel. The object comprises a bed, bed rail support, a pole, a support, a cable, an arm, a leg or an IV stand.

BRIEF DESCRIPTION OF THE DRAWINGS

For a more complete understanding of the features and advantages of the present invention, reference is now made to the detailed description of the invention along with the accompanying figures and in which:

FIG. 2 is a top view of one embodiment of the line manager of the present invention.

FIG. 3 is a top view of one embodiment of the line manager of the present invention.

FIG. 4 is a side view of one embodiment of the line manager of the present invention.

FIG. 5 is a side view of another embodiment of the line manager of the present invention.

FIG. 6 is a side view of one embodiment of the line manager of the present invention.

FIG. 7 is a side view of one embodiment of the line manager of the present invention in use.

FIG. 8 is a top view of one embodiment of the line manager of the present invention in use.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes a line manager to hold and removably secure within an aperture, one or more lines, or tubes adjacent to a patient, on or near a bed rail/rod, or other device. In some embodiments, the line manager is attached to a bed rail of a hospital, or medical bed and may be used to position and label the various tubes or lines going to the patient. The line manager may be made of a flexible material and can be a single use device or a multiple use device.

The present invention includes a line manager made from a flexible material including but not limited to a flexible elastomeric material. In addition the present invention may be constructed as a single piece or in separate pieces and assembled. Advantages of the present invention include reduced cost, increased reliability, consistent repeatability in manufacturing, and durability with no additional parts to maintain. In addition, the present invention may use a substrate material and design (empty space on "ear flaps") to label or mark tubing using a marker (SHARPIE®, etc.) or colored embodiment to mark and label with the patient's name, type of fluid/tube used, nurse's name, doctor's name, etc. In addition, the present invention includes a retention feature (loop) designed into the strap to force the unused portion of the strap to be neatly oriented down and away from the user to keep the long strap from getting in the way of the doctors and nurses along with being a convenient one-handed (pull down motion) way of securing the present invention. The present invention includes a designed to "tear-away" upon removal to allow for quick-emergency removal. In addition, this ensures that a new sanitized band is utilized for each patient to avoid the spreading of bacteria, etc.

Figure 1:
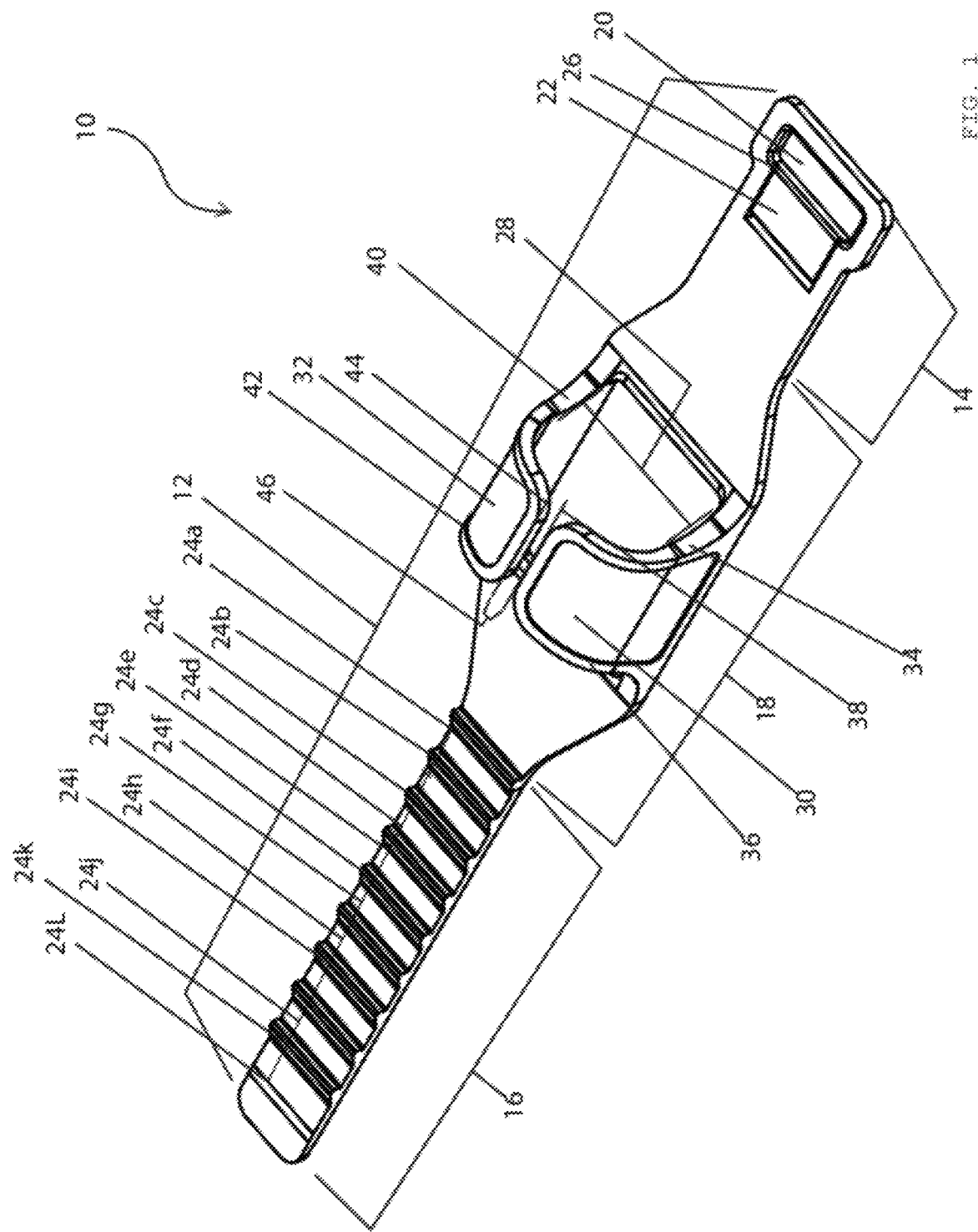
FIG. 1 is a perspective view of the line manager of the present invention.

FIG. 1 is a perspective view of the line manager 10 of the present invention. The line manager 10 is made of a flexible material to allow it to be secured to the bed rail such that the patient lines are positioned at, or above the patient and in some instances at, or above the top surface of the mattress. Alternatively, the line manager 10 may be attached to the patient directly or to a support located adjacent to the patient. The line manager 10 includes a strap 12 extending from a proximal end 14, and a distal end 16, separated by a body portion 18. The strap 12 is flexible and can be wrapped or positioned about a surface, body part, or rod. The proximal end 14 includes one or more slots 20 and 22. Although the embodiment in FIG. 1 depicts two slots 20 and 22, other embodiments may include 1, 2, 3, 4, 5, 6 etc., slots. In addition, the proximal end 14 may include a snap or a loop-and-hook fastener, or a combination thereof to secure the proximal end 14, and the distal end 16.

The distal end 16 extends to a length sufficient to encircle an object that is to be secured, and as such the length may vary between embodiments. The distal end 16 may optionally have one or more ridges 24a-24l extending from the surface of the distal end 16. The width of the distal end 16 is sized as to frictionally fit through the one or more slots 20 and 22. In embodiments with one or more ridges 24a-24l extending from the surface of the distal end 16, the one or more ridges 24a-24l contact the one or more slots 20 and 22 to frictionally secure the proximal end 14, and the distal end 16 about the object (not shown) to be secured. The distal end 16 may extend through the slot 20 and contact the divider 26 and further extend through the slot 22 such that the one or more ridges 24a-24l contact the divider 26 and secures the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28.

FIG. 2 is a top view of one embodiment of the line manager 10 of the present invention. The line manager 10 is made of a flexible material to allow it to be secured to the bed rail such that the patient lines are positioned at, or above the patient, and in some instances at, or above the top surface of the mattress. The line manager 10 includes a strap 12 extending from a proximal end 14 and a distal end 16 separated by a body portion 18. The strap 12 is flexible and can be wrapped or positioned about a surface or rod (not shown). The proximal end 14 includes one or more slots although the embodiment in FIG. 2 depicts one slot 20, other embodiments may include 1, 2, 3, 4, 5, etc., slots. In addition, the proximal end 14 may include a snap (not shown) or a loop-and-hook fastener (not shown) or a combination thereof to secure the proximal end 14 and the distal end 16. The distal end 16 extends to a length sufficient to encircle an object that is to be secured, and as such, the length may vary between embodiments. The distal end 16 may optionally have one or more ridges 24a-24l extending from the surface of the distal end 16. The width of the distal end 16 is sized as to frictionally fit through the slot 20. In embodiments with one or more ridges 24a-24l extending from the surface of the distal end 16, the one or more ridges 24a-24l contact the slot 20 to frictionally secure the proximal end 14 and the distal end 16 about the object (not shown). The distal end 16 may extend through the slot 20 such that the one or more ridges 24a-24l contact the slot 20 to secures the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28.

FIG. 3 is a top view of one embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots although the embodiment in FIG. 3 depicts one slot 22, other embodiments may include 1, 3, 4, 5, etc. slots. In addition, the proximal end 14 may include a snap (not shown) or a loop-and-hook fastener (not shown) or a combination thereof to secure the proximal end 14 and the distal end 16. The distal end 16 extends to a length sufficient to encircle an object that is to be secured, and as such, the length may vary between embodiments. The distal end 16 may optionally have one or more ridges 24a-24l extending from the surface of the distal end 16. The width of the distal end 16 is sized as to frictionally fit through the slot 22. In embodiments with one or more ridges 24a-24l extending from the surface of the distal end 16, the one or more ridges 24a-24l contact the slot 22 to frictionally secure the proximal end 14 and the distal end 16 about the object (not shown). The distal end 16 may extend through the slot 22 such that the one or more ridges 24a-24l contact the slot 22 to secure the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28.

FIG. 4 is a side view of one embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown). In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel 28 formed by a first tab 30 and a second tab 32. The first tab 30 includes a first proximal edge 34 and a first distal edge (not shown) separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some instances, the first edge 38 and the second edge 44 are overlapped to further secure the channel 28.

FIG. 5 is a side view of another embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown) although the embodiment in FIG. 1 depicts two slots (not shown), other embodiments may include 1, 2, 3, 4, 5, etc., slots. In addition, the proximal end 14 may include a snap (not shown) or a loop-and-hook fastener (not shown) or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). In embodiments with one or more ridges 24a-24i extending from the surface of the distal end 16, the one or more ridges 24a-24i contact the one or more slots (not shown) to frictionally secure the proximal end 14 and the distal end 16 about the object (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel (not shown) formed by a first tab 30 and a second tab (not shown). The first tab 30 includes a first proximal edge 34 and a first distal edge 36 separated by a first edge (not shown). Adjacent the first tab 30 is a second tab (not shown) that includes a second proximal edge (not shown) and a second distal edge (not shown) separated by a second edge (not shown). A channel aperture (not shown) is formed between the first edge (not shown) and the second edge (not shown). In some instances, the first edge (not shown) and the second edge (not shown) are overlapped to further secure the channel (not shown).

FIG. 6 is a side view of one embodiment of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown). In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel 28 formed by a first tab 30 and a second tab 32. The first tab 30 includes a first proximal edge 34 and a first distal edge (not shown) separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some instances, the first edge 38 and the second edge 44 are overlapped to further secure the channel 28.

FIG. 7 is a side view of one embodiment of the line manager 10 of the present invention in use. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. The proximal end 14 includes one or more slots (not shown). In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots (not shown). The distal end 16 may extend through the slot (not shown) and contact the divider (not shown) and further extend through the slot (not shown) such that the one or more ridges 24a-24i contact the divider (not shown) and secures the line manager 10. The body portion 18 includes a channel 28 formed by a first tab 30 and a second tab 32. The first tab 30 includes a first proximal edge 34 and a first distal edge (not shown) separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some instances, the first edge 38 and the second edge 44 are overlapped to further secure the channel 28.

FIG. 8 is a top view of one embodiment of the line manager 10 of the present invention in use. The line manager 10 is made of a flexible material to allow it to be secured to the bed rail such that the patient lines are positioned at or above the patient and in some instances at or above the top surface of the mattress. The line manager 10 includes a strap (not shown) extending from a proximal end 14 and a distal end 16 separated by a body portion 18. The strap (not shown) is flexible and can be wrapped or positioned about a surface or rod. The proximal end 14 includes one or more slots 20 and 22 although the embodiment in FIG. 8 depicts two slots 20 and 22, other embodiments may include 1, 2, 3, 4, 5, etc., slots. In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have one or more ridges 24a-24i extending from the surface of the distal end 16. The width of the distal end 16 is sized as to frictionally fit through the one or more slots 20 and 22. In embodiments with one or more ridges 24a-24i extending from the surface of the distal end 16, the one or more ridges 24a-24i contact the one or more slots 20 and 22 to frictionally secure the proximal end 14 and the distal end 16 about the object (not shown). The distal end 16 may extend through the slot 20 and contact the divider 26 and further extend through the slot 22 such that the one or more ridges 24a-24i contact the divider 26 and secures the line manager 10. The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge 42 separated by a second edge 44. A channel aperture 46 is formed between the first edge 38 and the second edge 44. In some instances, the first edge 38 and the second edge 44 are overlapped to further secure the channel 28.

Figure 9:
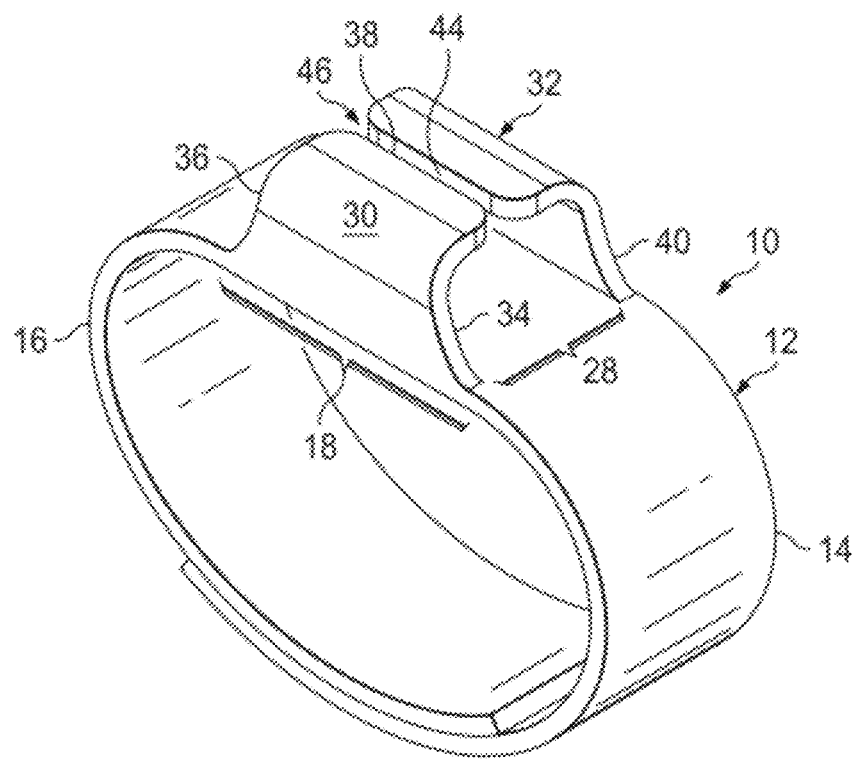
FIG. 9 is a perspective view of the line manager of the present invention.

FIG. 9 is a perspective view of the line manager 10 of the present invention. The line manager 10 is made of a flexible material to allow it to be secured to the bed rail such that the patient lines are positioned at or above the patient and in some instances at or above the top surface of the mattress. The line manager 10 includes a strap 12 extending from a proximal end 14 and a distal end 16 separated by a body portion 18. The strap 12 is flexible and can be wrapped or positioned about a surface or rod. In addition, the proximal end 14 may include a snap or a loop-and-hook fastener or a combination thereof to secure the proximal end 14 and the distal end 16. The distal end 16 extends to a length sufficient to encircle an object that is to be secured, and as such the length may vary between embodiments. The distal end 16 may optionally have a loop-and-hook fastener extending from the surface of the distal end 16 to frictionally secure the proximal end 14 and the distal end 16 about the object (not shown). The body portion 18 includes a channel 28 formed by a first tab 30 and a second tab 32. The first tab 30 includes a first proximal edge 34 and a first distal edge 36 separated by a first edge 38. Adjacent the first tab 30 is a second tab 32 that includes a second proximal edge 40 and a second distal edge (not shown) separated by a second edge 44. A channel aperture 46 is formed between the first edge 38 and the second edge 44. In some instances, the first edge 38 and the second edge 44 are overlapped to further secure the channel 28.

Figure 10A:
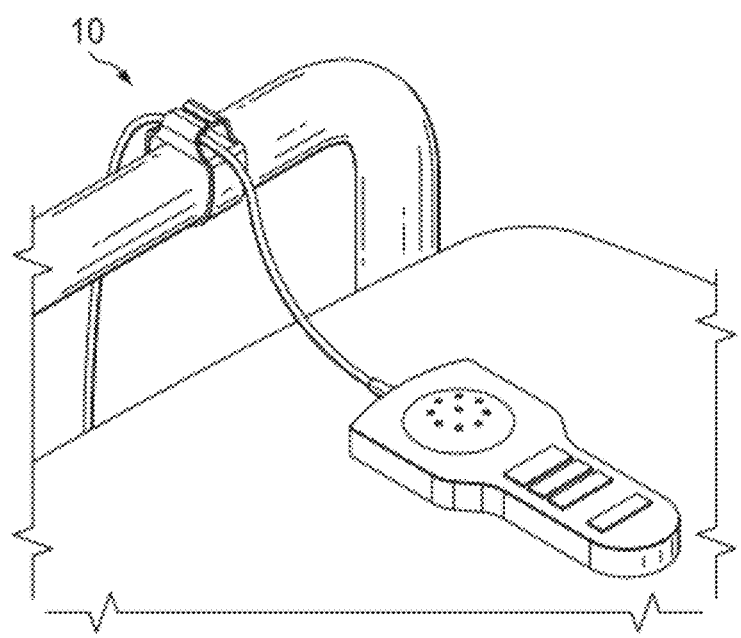
FIGS. 10a, 10b, 10c, and 10d are views of one embodiment of the line manager of the present invention in use.
Figure 10B:
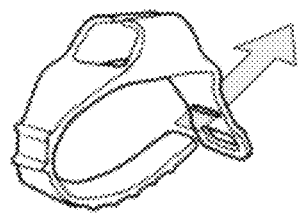
Figure 10C:
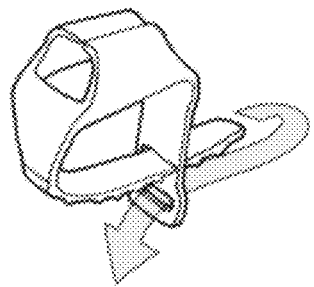
Figure 10D:
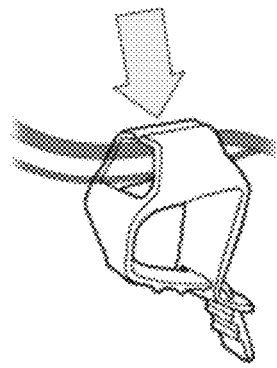

FIG. 10a is a view of one embodiment of the line manager 10 in use. FIG. 10b is an image of the line manager in operation where the line manager is placed around bedrail or stable fixture (not shown) and the notched end is inserted into upper thin slot on opposite end. FIG. 10c is an image of the line manager in use where the strap is pulled through until tight to lock line manager in place. The lower slot is fed through to direct the end down and out of the way. FIG. 10d is an image of the line manager in use where the feed tubes, cables, and cords are placed through the large clasp on top for organization, accessibility, and safety.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A line management device for attaching to a fixture wherein the line management device comprises:
   two or more patient care lines;
   a flexible strap comprising a proximal strap end comprising one or more slots positioned through a portion of the proximal strap end;
   a body portion connected to the proximal strap end, wherein the body portion comprises:
   a channel positioned on top of the flexible strap:
   wherein the channel is formed by (a) a bottom located under the two or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the bottom and the first curved flexible tab and the adjacent second curved flexible tab form the channel, wherein the first curved flexible tab and the adjacent second curved flexible tab form an opening that is more narrow than each of the two or more patient care lines;
   wherein the channel is sized to allow the two or more patient care lines to be simultaneously placed within the channel and the channel simultaneously retains the two or more patient care lines without longitudinally restraining the two or more patient care lines between the first curved flexible tab, the adjacent second curved flexible tab and the bottom of the channel; and
   a distal strap end connected to the body portion, wherein the distal strap end extends through the one or more slots to secure the distal strap end to the proximal strap end.

2. The line management device of claim 1, wherein the flexible strap is rubber.

3. The line management device of claim 1, wherein the channel is parallel to the proximal strap end.

4. The line management device of claim 1, wherein the channel is perpendicular to the proximal strap end.

5. The line management device of claim 1, wherein the first curved tab and the adjacent second curved tab overlap.

6. A line management device for removably simultaneously retaining two or more patient care lines, wherein the line management device comprises:
   two or more patient care lines;
   a flexible strap comprising a proximal strap end that comprises a securing mechanism;
   a body portion connected to the proximal strap end, wherein the body portion comprises:
   a channel positioned on top of the flexible strap wherein the channel is formed by (a) a bottom located under the two or more patient care lines, wherein the bottom is formed from the body portion, (b) a first curved flexible tab that extends from the body portion and curves towards (c) an adjacent second curved flexible tab that extends from the body portion and curves towards the first curved flexible tab, wherein the first curved flexible tab and the adjacent second curved flexible tab overlap or form an opening that is more narrow than each of the two or more patient care lines;
   wherein the channel allows the two or more patient care lines to be removably simultaneously placed within the channel and the channel removably and simultaneously retains the two or more patient care lines without the two or more patient care lines being longitudinally restrained between the first curved flexible tab, the second adjacent curved flexible tab and the bottom of the channel; and
   a distal strap end connected to the body portion, wherein the distal strap end comprises a connection mechanism that engages the securing mechanism of the proximal strap end to removably secure the proximal strap end to the distal strap end.

7. The line management device of claim 6, wherein the channel is parallel to the proximal strap end.

8. The line management device of claim 6, wherein the channel is perpendicular to the proximal strap end.

9. The line management device of claim 6, wherein the first curved tab and the adjacent second curved tab overlap.

10. The line management device of claim 6, wherein the securing mechanism comprises a hook closure and the connection mechanism comprises a loop closure to mate the securing mechanism and the connection mechanism.

11. The line management device of claim 6, wherein the securing mechanism comprises a loop closure and the connection mechanism comprises a hook closure to mate the securing mechanism and the connection mechanism.

12. The line management device of claim 6, wherein the securing mechanism comprises a tab closure and the connection mechanism comprises an aperture closure to mate the securing mechanism and the connection mechanism.

13. The line management device of claim 6, wherein the securing mechanism comprises an aperture closure at the proximal strap end and the connection mechanism comprises a tab closure at the distal strap end to mate the securing mechanism and the connection mechanism.

14. The line management device of claim 6, wherein the securing mechanism comprises one or more slots at the distal strap end and the connection mechanism comprises a tab at the proximal strap end, wherein the tab extends through the one or more slots to secure the securing mechanism and the connection mechanism.

15. The line management device of claim 6, wherein the securing mechanism comprises a tab at the proximal strap end and the connection mechanism comprises one or more slots at the distal strap end, wherein the tab extends through the one or more slots to secure the securing mechanism and the connection mechanism.

16. The line management device of claim 15, wherein the tab comprises one or more ridges to fit the securing mechanism and the connection mechanism.

17. A line management device for attaching to a fixture wherein the line management device comprises:
   two or more patient care lines;
   a flexible strap comprising a proximal strap end that is connected to a distal strap end by a body portion, wherein the proximal strap end comprises a securing mechanism and the distal strap end comprises a connection mechanism, wherein the securing mechanism and the connection mechanism operate to secure the flexible strap around the fixture;
   wherein the body portion comprises:
   a channel positioned on top of the body portion of the flexible strap wherein the channel is formed by (a) a bottom under the two or more patient care lines, wherein the bottom is formed from the body portion, (b) a first curved flexible tab that extends from the body portion and curves toward (c) an adjacent second curved flexible tab that extends from the body portion and curves towards the first curved flexible tab, wherein the first curved flexible tab and the adjacent second curved flexible tab overlap;

wherein the channel allows the two or more patient care lines to be removably simultaneously placed within the channel and the channel removably and simultaneously retains the two or more patient care lines without the two or more patient care lines being longitudinally restrained between the first curved flexible tab, the second adjacent curved flexible tab and the bottom of the channel.

18. The line management device of claim 17, wherein the two or more patient care lines comprise two to four patient care lines.

\* \* \* \* \*